United States Patent
Dalko et al.

(10) Patent No.: US 6,548,532 B2
(45) Date of Patent: *Apr. 15, 2003

(54) INDOLECARBOXYLIC COMPOUNDS FOR TREATING SEBORRHEA AND COMPLICATIONS THEREOF

(75) Inventors: Maria Dalko, Gif S/Yvette (FR); Jean-Baptiste Galey, Aulnay-Sous-Bois (FR); Bruno Bernard, Neuilly sur Seine (FR)

(73) Assignee: Societe L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/000,293

(22) Filed: Dec. 4, 2001

(65) Prior Publication Data
US 2002/0058680 A1 May 16, 2002

Related U.S. Application Data

(62) Division of application No. 09/617,039, filed on Jul. 14, 2000, now Pat. No. 6,335,359.

(30) Foreign Application Priority Data

Jul. 16, 1999 (FR) .............................. 99 09269

(51) Int. Cl.⁷ .................... A61K 31/405; A61K 31/40; A61K 7/00; C07D 411/00; C07D 209/52; C09K 3/00
(52) U.S. Cl. .................... 514/415; 424/401; 514/429; 548/454; 548/516; 252/380
(58) Field of Search ................ 514/415, 429; 424/401; 548/454, 516; 252/380

(56) References Cited

U.S. PATENT DOCUMENTS

| 5,342,547 A | 8/1994 | Konya et al. |
| 5,767,139 A | 6/1998 | Maw et al. |
| 5,912,357 A | 6/1999 | Blagg et al. |

FOREIGN PATENT DOCUMENTS

| EP | 0 565 417 A1 | * 10/1993 |
| WO | WO 99/07351 A2 | 2/1999 |
| WO | WO 99/12905 A1 | 3/1999 |

OTHER PUBLICATIONS

D.A. Holt et al., "Benzophenone– and Indolecarboxylic acids: potent type–2 specific inhibitors of human steroid 5 alpha–reductasel", Journal of Medicinal Chemistry, vol. 38, No. 1, 1992, pp 13–14, XP002068506, Washington US p. 13, colonne de gauche, lines 1–11, Table 2.

Black et al, Aust. J. Chem., 1986, 39, 15–20, "Synthesis of 4,6–Dimethoxyindoles".

Pragger et al., Aust. J. Chem., 1996, 49, 131501323, "The Chemistry of 5–Oxodihydroisoxazoles . . . ".

Tani et al., Heterocycles, 1992, 34(12), 2349–2362, "Regioselective Bromination of Methoxy Derivativew of Ethyl Indole–Carboxylate . . . ".

Allen et al., Synth. Comm., 1992, 22(14), 2077–2102, "Entry into 6–Methoxy–D(+)–Tryptophans . . . ".

Copy of Search Report issued May 10, 2000 in French Application No. FR 9909269.

* cited by examiner

Primary Examiner—Sreeni Padmanabhan
Assistant Examiner—Michael A. Willis
(74) Attorney, Agent, or Firm—Burns, Doane, Swecker & Mathis, L.L.P.

(57) ABSTRACT

Indolecarboxylic acid compounds and derivatives thereof are useful for treating seboarhea and the dermatitides associated therewith, especially acne and/or blackheads and/or comedones.

7 Claims, No Drawings

INDOLECARBOXYLIC COMPOUNDS FOR TREATING SEBORRHEA AND COMPLICATIONS THEREOF

This application is a divisional of application Ser. No. 09/617,039, filed on Jul. 14, 2000, now U.S. Pat. No. 6,335,359.

CROSS-REFERENCE TO PRIORITY APPLICATION

This application claims priority under 35 U.S.C. §119 of FR-99/09269, filed Jul. 16, 1999, hereby expressly incorporated by reference.

BACKGROUND OF THE INVENTION

1. Technical Field of the Invention

The present invention relates to novel cosmetic/dermatological compositions containing a therapeutically effective amount of 4,6-dimethoxyindole-2-carboxylic acid or derivatives thereof, for treating seborrhoea and the dermatitides associated therewith, in particular acne and/or blackheads and/or comedones.

2. Description of the Prior Art

Seborrhoea or sebaceous hypersecretion is the cause of skin disorders such as greasy skin and a greasy scalp, these aesthetic disorders potentially becoming a source for dermatological afflictions/conditions such as acne, seborrhoeic dermatitis, blackheads or comedones.

Acne is one of the conditions usually affecting, and to varying degrees, the juvenile population between 15 and 30 years old. Acne is essentially the consequence of two interlinked phenomena: sebaceous hypersecretion and disruption of the keratinization of the pilosebaceous follicles, the consequences of which are obstruction of the pilosebaceous follicles and the formation of retentive lesions or comedones. Following microbial proliferation, the comedones can develop into inflammatory lesions, papules and pustules.

Seborrhoeic dermatitis is associated with the proliferation of yeasts of the Pityrosporum genus on the sebum which constitutes their substrate.

In the case of both acne and seborrhoeic dermatitis, regulating the sebaceous flux eliminates the initial cause, i.e., the excessive presence of sebum; and consequently treats the dermatitis.

This is what is observed with isotretinoin, the oral administration of which induces drying-out of the sebaceous follicles and leads to disappearance of the symptoms.

However, the administration of isotretinoin is not without serious side effects and consequently remains reserved for the treatment of severe, incapacitating acne. Topical treatments of seborrhoea have hitherto proven to be relatively ineffective, and this lack of efficacy is frequently overcome by means of systemic treatments, in particular with isotretinoin or anti-androgenic products.

Thus, serious need continues to exist for topical active agents which favorably influence sebaceous hypersecretion and consequently the dermatitides associated therewith.

SUMMARY OF THE INVENTION

It has now surprisingly and unexpectedly been determined that 4,6-dimethoxyindole-2-carboxylic acid and derivatives thereof exhibit antiseborrhoeic properties and are thus useful active agents for combating seborrhoea of the skin or the scalp, and for combating the dermatitides which may result therefrom, such as acne, seborrhoeic dermatitis, blackheads and/or comedones.

Briefly, the present invention features cosmetic/dermatological compositions comprising a therapeutically effective antiseborrhoeic amount of at least one compound having the structural formula (I):

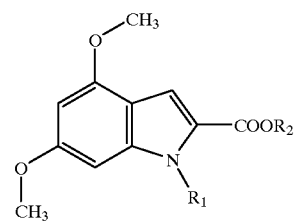

in which $R_1$ and $R_2$, which may be identical or different, are each a hydrogen atom; a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle; the acylated derivatives or the physiologically acceptable salts thereof, either singly or in any admixture; for treating seborrhoea of the skin and/or the scalp, and/or the dermatitides associated with seborrhoea.

DETAILED DESCRIPTION OF BEST MODE AND SPECIFIC/PREFERRED EMBODIMENTS OF THE INVENTION

More particularly according to the present invention, the dermatitis associated with seborrhoea can be, especially acne, and/or blackheads and/or comedones.

The subject compounds exhibit marked utility as active principles for preventively and/or curatively treating seborrhoea of the skin and/or the scalp, as well as the dermatitides associated with seborrhoea, such as acne and/or blackheads and/or comedones.

It was hitherto unknown to use such compounds to treat seborrhoea of the skin and/or the scalp, and the dermatitides associated with seborrhoea, such as acne and/or blackheads and/or comedones has never been proposed in the prior art.

According to this invention, by the term "heterocycle" is preferably intended a ring optionally including one or more nitrogen and/or oxygen atoms and more particularly pyridine, imidazole, tetrahydrofuran or furan. One heterocycle which is particularly preferred according to the invention is pyridine.

By the expression "$C_1$–$C_4$ alkyl radical" are intended linear or branched acyclic radicals having from 1 to 4 carbon atoms, derived from the removal of a hydrogen atom from a hydrocarbon molecule, and in particular methyl, ethyl, propyl, isopropyl, butyl, isobutyl or tert-butyl radicals.

By the expression "$C_7$–$C_{12}$ aralkyl radical" are preferably intended alkylaryl radicals having from 7 to 12 carbon atoms, in which definition the term "aryl" connotes an aromatic ring containing 5 or 6 carbon atoms or an aromatic heterocycle containing 5 or 6 atoms. According to the invention, the aralkyl radical is preferably $C_7$–$C_{10}$. One aralkyl radical which is particularly preferred according to the invention is the benzyl radical.

And by the expression "optionally substituted phenyl radical" is preferably intended a phenyl radical optionally substituted with a cyano (—CN) group, a trifluoromethyl (—CF$_3$) group, a methoxy (—O—CH$_3$) group or a halogen atom. The halogen atom can be selected from among chlorine, bromine, fluorine and iodine. One substituted phenyl radical which is particularly preferred according to the invention is a phenyl radical substituted with a trifluoromethyl (—CF$_3$) group.

In one preferred embodiment of the invention, R$_1$ is a hydrogen atom or a methyl or ethyl radical.

In another preferred embodiment of the invention, R$_2$ is a hydrogen atom or a methyl radical.

And in a very preferred embodiment of the invention, R$_1$ and R$_2$ are each a hydrogen atom.

Exemplary compounds of formula (I) include:
4,6-dimethoxyindole-2-carboxylic acid;
methyl 4,6-dimethoxyindole-2-carboxylate;
N-methyl-4,6-dimethoxyindole-2-carboxylic acid;
methyl N-methyl-4,6-dimethoxyindole-2-carboxylate;
N-ethyl-4,6-dimethoxyindole-2-carboxylic acid.

Among these compounds, that most particularly preferred is 4,6-dimethoxyindole-2-carboxylic acid.

According to the invention, the subject compounds can be used alone or as a mixture.

It will of course be appreciated that the effective amount of compound to be administered corresponds to the amount required to elicit the desired result. One skilled in this art is thus capable of evaluating this effective amount, which depends on the nature of the compound and on the individual thus treated. To provide an order of magnitude, in the compositions according to the invention the compound of formula (I) is typically present in a concentration ranging from 0.001% to 20% by weight relative to the total weight of the composition and preferably from 0.1% to 5%.

According to the present invention, the compounds of formula (I) can be formulated into any suitable medium (vehicle, diluent or carrier) for cosmetic and pharmaceutical applications. The compounds of formula (I) are preferentially formulated into compositions for cosmetic application.

The compositions according to the invention can be in any form which is suitable for topical application, in particular in the form of aqueous, aqueous/alcoholic or oily solutions, dispersions of the lotion or serum type, aqueous, anhydrous or oily gels, ointments, emulsions of liquid or semi-liquid consistency of the milk type, obtained by dispersing a fatty phase in an aqueous phase (O/W) or, conversely, (W/O), suspensions or emulsions of soft, semi-solid or solid consistency of the cream or gel type, microemulsions, or alternatively microcapsules, microparticles or vesicular dispersions of ionic and/or nonionic type. These compositions are formulated via the usual techniques that are well known to this art.

The compositions of the invention can comprise the additives and adjuvants conventionally formulated in the field under consideration, such as fatty substances, organic solvents, thickeners, softeners, antioxidants, opacifiers, stabilizers, antifoaming agents, fragrances, ionic or nonionic emulsifiers, fillers, sequestering agents, dyes, colorants or any other ingredient usually included in cosmetics.

When the composition of the invention is an emulsion, the proportion of the fatty phase can range from 5% to 80% by weight, and preferably from 5% to 50% by weight, relative to the total weight of the composition. The oils, the emulsifiers and the co-emulsifiers included in the composition in emulsion form are selected from among those conventional in cosmetics or dermatology. The emulsifier and optionally the co-emulsifier are advantageously present in the composition in a proportion ranging from 0.3% to 30% by weight, and preferably from 0.5% to 20% by weight, relative to the total weight of the composition. The emulsion can also contain lipid vesicles.

Exemplary oils according to the invention, include mineral oils (liquid petroleum jelly), plant oils (liquid fraction of karite butter), animal oils, synthetic oils (purcellin oil, hydrogenated polyisobutene), silicone oils and fluoro oils (perfluoropolyethers). Fatty alcohols, fatty acids and waxes are also exemplary fatty substances.

Exemplary emulsifiers according to the invention include fatty acid esters of polyols, such as fatty acid esters of sorbitol, for instance sorbitan tristearate marketed under the trademark Span 65 by ICI, or fatty esters of glycerol such as glyceryl monostearate, or else PEG esters such as PEG-40 stearate marketed under the trademark Myrj 52 by ICI. Also exemplary are silicone emulsifiers such as cetyl dimethicone copolyol marketed under the trademark Abil EM90 by Goldschmidt.

And exemplary hydrophilic gelling agents include carboxyvinyl polymers (carbomer), acrylic copolymers such as acrylate/alkylacrylate copolymers, polyglyceryl (meth) acrylates such as the product marketed under the trademark Norgel by Guardian, polyacrylamides and in particular the mixture of polyacrylamide, C13–14-isoparaffin and Laureth-7, marketed under the trademark Sepigel 305 by Seppic, polysaccharides, natural gums and clays, and exemplary lipophilic gelling agents include modified clays, for instance bentones, metal salts of fatty acids, hydrophobic silica and polyethylenes.

The compositions of the invention can also comprise hydrophilic or lipophilic biologically active agents, in particular active agents capable of complementing the effect of ascorbic acid in the treatment of seborrhoea and the associated dermatitides, and in particular acne. These include, for example, anti-inflammatory agents such as benzoyl peroxide, antibiotics, antiseptic agents such as octopirox or keratolytic active agents such as salicylic acid and derivatives thereof, alpha-hydroxy acids, retinoic acid and derivatives thereof, and retinol and derivatives thereof.

Hydrophilic active agents which are exemplary include proteins or protein hydrolysates, amino acids, polyols (glycerol, propylene glycol), urea, allantoin, sugars and sugar derivatives, water-soluble vitamins, starch, bacterial or plant extracts, in particular Aloe Vera, and moisturizers.

And lipophilic active agents include tocopherol (vitamin E) and derivatives thereof, essential fatty acids, ceramides and essential oils.

The present invention also features a cosmetic regime/regimen for treating seborrhoea and the dermatitides associated with seborrhoea, such as, for example, acne and/or blackheads and/or comedones, comprising topically applying onto the skin and/or the scalp a composition containing a therapeutically effective amount of at least one compound having the structural formula (I), maintaining such composition in contact with the skin and/or the scalp, and optionally rinsing same therefrom.

The cosmetic regimen/regimen of the invention is preferentially for treating acne and/or blackheads and/or comedones.

Such treatment has the characteristics of cosmetic methodology since it improves the aesthetics of the skin by rendering it better in appearance.

In order to further illustrate the present C invention and the advantages thereof, the following specific examples are given, it being understood that same are intended only as illustrative and in nowise limitative.

In said examples to follow, each is a specific formulation according to the invention, and each was formulated via conventional cosmetics or pharmacy technique.

EXAMPLE 1

Niosomal Gel:

| | |
|---|---|
| Chimexane NS ® | 1.80 g |
| Monosodium stearoylglutamate | 0.20 g |
| 4,6-Dimethoxyindole-2-carboxylic acid | 1.00 g |
| Carbomer | 0.20 g |
| Triethanolamine | qs pH = 7 |
| Preservatives | qs |
| Fragrances | qs |
| Demineralized water | qs 100.00 g |

This gel is applied to the skin once or twice a day.

EXAMPLE 2

Niosomal Lotion:

| | |
|---|---|
| Chimexane NL ® | 0.475 g |
| Cholesterol | 0.475 g |
| Monosodium stearoylglutamate | 0.050 g |
| 4,6-Dimethoxyindole-2-carboxylic acid | 2.000 g |
| Preservatives | qs |
| Dyes | qs |
| Fragrance | qs |
| Demineralized water | qs 100.00 g |

This lotion is applied to the skin once or twice a day.

EXAMPLE 3

Lotion:

| | |
|---|---|
| 4,6-Dimethoxyindole-2-carboxylic acid | 2.00 g |
| Dowanol PM ®** | 20.00 g |
| Klucel G ®** | 3.00 g |
| Ethyl alcohol | 40.00 g |
| Water | qs 100.00 g |

1 ml of this lotion is applied to the skin at a frequency of once or twice a day.
*Hydroxypropylcellulose marketed by Hercules
**Propylene glycol monomethyl ether marketed by Dow Chemical While the invention has been described in terms of various specific and/or preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic or dermatological composition comprising a cosmetically or therapeutically effective amount of at least one indolecarboxylic acid compound or ester or salt thereof, formulated into a topically applicable, cosmetically or dermatologically acceptable vehicle, diluent or carrier therefor, said at least one indolecarboxylic acid compound having the structural formula (I):

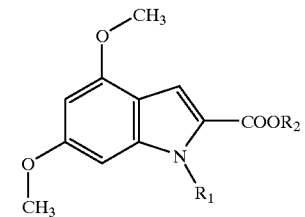

(I)

in which $R_1$ and $R_2$, which may be identical or different, are each a hydrogen atom; a $C_1$–$C_6$ alkyl radical, optionally substituted with an —OH, —$NRR_3$, —SH, —COOH or —$COOR_3$ radical, wherein $R_3$ is a linear or branched $C_1$–$C_4$ alkyl radical; a $C_7$–$C_{12}$ aralkyl radical;

or a radical —$CHR_4R_5$ wherein $R_4$ and $R_5$, which may be identical or different, are each a hydrogen atom, an optionally substituted phenyl radical, or a 5- or 6-membered heterocycle; or an acylated derivative or physiologically acceptable salt thereof;

wherein said cosmetic or dermatological composition is suitable for treating seborrhea and/or the dermatitides associated therewith, and is in the form of an aqueous, aqueous/alcoholic, or oily solution, dispersion, serum, milk, ointment, emulsion, gel, cream, microemulsion, suspension, microcapsules, microparticles, or vesicular dispersion.

2. The cosmetic or dermatological composition as defined by claim 1, comprising from 0.001% to 20% by weight of said at least one compound having the structural formula (I).

3. The cosmetic or dermatological composition as defined by claim 2, comprising from 0.1% to 5% by weight of said at least one compound having the structural formula (I).

4. The cosmetic or dermatological composition as defined by claim 1, further comprising a fatty substance, organic solvent, thickener, softener, antioxidant, opacifier, stabilizer, antifoaming agent, fragrance, ionic or nonionic emulsifier, filler, sequestering agent, dye or colorant, or combination thereof.

5. The cosmetic or dermatological composition as defined by claim 1, further comprising a hydrophilic or lipophilic agent.

6. The cosmetic or dermatological composition as defined by claim 5, further comprising an anti-inflammatory agent, antibiotic, antiseptic agent, keratolytic active agent, alpha-hydroxy acid, retinoic acid, retinol, or combination thereof.

7. The cosmetic or dermatological composition as defined by claim 5, further comprising a protein or protein hydrolysate, amino acid, polyol, urea, allantoin, sugar, water-soluble vitamin, starch, bacterial or plant extract, moisturizer, tocopherol, essential fatty acid, ceramide, essential oil, or combination thereof.

* * * * *